(12) United States Patent
Teucher et al.

(10) Patent No.: US 11,517,680 B2
(45) Date of Patent: Dec. 6, 2022

(54) INJECTION DEVICE WITH AN ACOUSTIC FEEDBACK ARRANGEMENT

(71) Applicant: SANOFI, Paris (FR)

(72) Inventors: Axel Teucher, Frankfurt am Main (DE); Michael Jugl, Frankfurt am Main (DE); Stefan Blancke, Frankfurt am Main (DE)

(73) Assignee: Sanofi, Paris (FR)

( * ) Notice: Subject to any disclaimer, the term of this patent is extended or adjusted under 35 U.S.C. 154(b) by 480 days.

(21) Appl. No.: 16/492,790

(22) PCT Filed: Mar. 12, 2018

(86) PCT No.: PCT/EP2018/056029
§ 371 (c)(1),
(2) Date: Sep. 10, 2019

(87) PCT Pub. No.: WO2018/166951
PCT Pub. Date: Sep. 20, 2018

(65) Prior Publication Data
US 2020/0054835 A1 Feb. 20, 2020

(30) Foreign Application Priority Data

Mar. 14, 2017 (EP) .................... 17305270

(51) Int. Cl.
*A61M 5/315* (2006.01)
*A61M 5/31* (2006.01)
*A61M 5/24* (2006.01)

(52) U.S. Cl.
CPC ........ *A61M 5/3157* (2013.01); *A61M 5/2422* (2013.01); *A61M 5/3158* (2013.01);
(Continued)

(58) Field of Classification Search
CPC ............ A61M 5/3157; A61M 5/31551; A61M 5/3158; A61M 5/2422; A61M 2005/3126; A61M 2205/581
See application file for complete search history.

(56) References Cited

U.S. PATENT DOCUMENTS 6,543,574 B1  4/2003 Zone et al.
2004/0210199 A1* 10/2004 Atterbury ............ G01D 5/2497
604/224

(Continued)

FOREIGN PATENT DOCUMENTS

CA    2760237    11/2010
CN    1296721    5/2001
(Continued)

OTHER PUBLICATIONS

International Preliminary Report on Patentability in International Application No. PCT/EP2018/059029, dated Sep. 17, 2019, 9 pages.

(Continued)

*Primary Examiner* — Tasnim Mehjabin Ahmed
(74) *Attorney, Agent, or Firm* — Fish & Richardson P.C.

(57) ABSTRACT

An injection device for setting and injecting of a dose of a medicament includes: an acoustic feedback arrangement comprising: a first feedback element having a first engaging section and having a free end section located at a predetermined distance from the first engaging section, a second feedback element having a second engaging section configured to engage with the first engaging section, wherein the first feedback element is movable, pivotable or resiliently deformable along a first direction (d1) relative to the second feedback element from an initial state (i) towards a biased
(Continued)

state (b), and a sound generator formed by the first engaging section or audibly engageable with the free end section of the first feedback element.

17 Claims, 3 Drawing Sheets

(52) U.S. Cl.
CPC . *A61M 5/31551* (2013.01); *A61M 2005/3126* (2013.01); *A61M 2205/581* (2013.01)

(56) References Cited

U.S. PATENT DOCUMENTS

| | | | | |
|---|---|---|---|---|
| 2009/0012479 | A1* | 1/2009 | Moller | A61M 5/20 604/211 |
| 2016/0030678 | A1 | 2/2016 | Bayer et al. | |
| 2016/0250418 | A1 | 9/2016 | Olson | |
| 2016/0354548 | A1 | 12/2016 | Moller et al. | |

FOREIGN PATENT DOCUMENTS

| | | |
|---|---|---|
| CN | 1422140 | 6/2003 |
| CN | 101107032 | 1/2008 |
| CN | 102089023 | 6/2011 |
| CN | 102510762 | 6/2012 |
| CN | 104080499 | 10/2014 |
| CN | 105102044 | 11/2015 |
| CN | 109172948 | 1/2019 |
| DE | 102015000999 | 7/2016 |
| JP | 2008-528144 | 7/2008 |
| JP | 2015-213823 | 12/2015 |
| WO | WO 2001/076520 | 10/2001 |
| WO | WO 2004/078239 | 9/2004 |
| WO | WO 2004/078240 | 9/2004 |
| WO | WO 2004/078241 | 9/2004 |
| WO | WO 2006/079481 | 8/2006 |
| WO | WO 2009/141650 | 11/2009 |
| WO | WO 2010/026580 | 3/2010 |
| WO | WO 2011/019777 | 2/2011 |
| WO | WO 2011/036133 | 3/2011 |
| WO | WO 2013/057033 | 4/2013 |
| WO | WO 2016/001304 | 1/2016 |
| WO | WO 2016/055438 | 4/2016 |
| WO | WO 2016/089871 | 6/2016 |
| WO | WO 2016/091843 | 6/2016 |
| WO | WO 2018/166951 | 9/2018 |

OTHER PUBLICATIONS

International Search Report and Written Opinion in International Application No. PCT/EP2018/056029, dated Jun. 15, 2018, 12 pages.

* cited by examiner

INJECTION DEVICE WITH AN ACOUSTIC FEEDBACK ARRANGEMENT

CROSS-REFERENCE TO RELATED APPLICATIONS

The present application is the national stage entry of International Patent Application No. PCT/EP2018/056029, filed on Mar. 12, 2018, and claims priority to European Application No. EP 17305270.5, filed on Mar. 14, 2017, the disclosures of which are incorporated herein by reference.

TECHNICAL FIELD

The present disclosure relates to an injection device with an acoustic feedback arrangement. In one aspect, the disclosure relates to a hand held injection device, such as pen-type injector for setting and dispensing of a dose of a medicament. The injection device is equipped with an acoustic feedback arrangement to provide acoustic and audible feedback to a user when using the injection device. The acoustic feedback arrangement is particularly dedicated to provide an audible and hence an acoustic signal at the end of a dose dispensing procedure conducted and executed by the injection device.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such as diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, the dose setting and the dose dispensing procedure must be easy to operate and has to be unambiguous.

Typically, such devices comprise a housing including a particular cartridge holder, adapted to receive a cartridge at least partially filled with the medicament to be dispensed. Such devices further comprise a drive mechanism, usually having a displaceable piston rod which is adapted to operably engage with a piston or bung of the cartridge. By means of the drive mechanism and its piston rod, the bung or piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in a distal direction by means of a pierceable seal and being further sealed in proximal direction by the bung. With reusable injection devices an empty cartridge is replaceable by a new one. In contrast, injection devices of disposable type are to be discarded when the medicament in the cartridge has been dispensed or used-up.

During an injection procedure the medicament expelled through an injection needle is injected into biological tissue of the patient. In order to ensure a complete administering of a dose of the medicament it is required to keep the needle for a while in the injection site of the biological tissue after the dose dispensing process is terminated. Typically, the patient has to wait for a predetermined hold time, e.g. a few seconds, before the injection needle can be withdrawn from the tissue. For this but also in general it is desirable to audibly indicate to the user of the device when the process of dose dispensing has terminated.

Known devices may provide a particular sound or a klick signal as an indication that the complete dose has been administered.

Especially with purely mechanically implemented injection devices a particular end of dose sound produced by the device may be difficult to perceive, especially for patients suffering a hearing loss. It is therefore desirable to improve the acoustic properties of an injection device especially in terms of an acoustic or audibly perceivable end of dose indication. The injection device should provide a clear and distinct sound or an acoustic signal at the end of a dose dispensing procedure. For this, the injection device should provide an acoustic feedback arrangement that is easy and straightforward to implement, even with existing designs of injection devices. The feedback arrangement should provide a simple and cost efficient approach to improve the audible and acoustic feedback of the injection device.

SUMMARY

In one aspect an injection device is provided for setting and injecting of a dose of a medicament. The injection device comprises an acoustic feedback arrangement. The acoustic feedback arrangement comprises a first feedback element having a first engaging section and further having a free end section that is located at a predetermined distance from the first engaging section. The acoustic feedback arrangement further comprises a second feedback element having a second engaging section that is configured to engage with the first engaging section. The first and the second engaging sections are configured to mechanically engage, i.e. to get in mutual mechanical contact.

The first feedback element is movable, pivotable or resiliently deformable along a first direction relative to the second feedback element. The first feedback element is movable, pivotable or resiliently deformable from an initial state towards a biased state. The acoustic feedback arrangement further comprises a sound generator that is either formed by the first engaging section or which is audibly engageable with the free end section of the first feedback element. When audibly engageable with the free end section of the first feedback element the sound generator may be provided as a separate part from the first feedback element. It may be connected to or may be integrated into the second feedback element. When the sound generator is formed by the first engaging section, the sound generator is integrated into the first feedback element.

When the sound generator is exclusively formed and provided by the first engaging section the free end section of the first feedback element provides an acoustic amplification of the sound generated by the sound generator. In some embodiments the free end section is free to vibrate and may hence amplify an acoustically perceivable sound generated by the mutual engagement of the first engaging section and the second engaging section of first and second feedback elements, respectively. Consequently and due to the acoustic amplification provided by the free end section of the first feedback element a sound pressure or a loudness of the sound generated by the mutual interaction of the first and the second engaging sections can be increased compared to solutions wherein a free end section of a first feedback element is audibly engaged with a second feedback element.

In some embodiments, wherein the sound generator is formed and provided by a separate part of the acoustic feedback arrangement or of the injection device the free end section of the first feedback element provides and behaves as a clapper, as a tongue or as a mallet, temporally mechanically and acoustically engaging with the sound generator. Here, the free end section of the first feedback element is configured to strike the sound generator in order to produce a well-defined audible and acoustically perceivable feedback signal or feedback sound.

In some examples, the first engaging section is configured to audibly engage with the second engaging section when the first feedback element returns from the biased state to the initial state. In the biased state the first feedback element may be pre-tensed or biased compared to the initial state, in which the first feedback element may be in a relaxed state. The first feedback element may be resiliently deformable against a restoring force from the initial state towards the biased state. When released from the biased state the first feedback element may return into the initial state under the effect of the restoring force. In some examples, the first feedback element may be relatively stiff and rigid. It may be then pivotally or movably arranged relative to the second feedback element. Then, the first feedback element may be pivotable or displaceable against a restoring force from the initial state to the biased state. The first feedback element may be engaged with a restoring element, such as a spring element, providing a restoring force to displace or to pivot the first feedback element from the biased state to the initial state.

The first engaging section and the second engaging section are complementary or correspondingly shaped so as to generate a well-defined and specific audible and acoustically perceivable signal when the first feedback element returns from the biased state to the initial state. In the initial state or prior to reaching the initial state the first engaging section and the second engaging section mechanically and audibly engage.

According to some examples, the free end section of the first feedback element is free of contact to any other component of the injection device or of the acoustic feedback arrangement when the first feedback element is in the initial state. When in the initial state, the first engaging section and the second engaging section may be in mutual abutment but the free end section of the first feedback element is contactless to any other component of the acoustic feedback arrangement or of the injection device. In this way, the free end section of the first feedback element is enabled to vibrate substantially undamped or unmuted. An acoustic noise or acoustic sound generated by the mechanical interaction of the first engaging section and the second engaging section may propagate towards the free end section of the first feedback element and may emanate therefrom to the environment. The contactless mounting or suspension of the free end section inside the injection device provides an acoustic amplification of an acoustic signal generated by the mechanical engagement of the first and second engaging sections of the first and the second feedback elements.

In some examples, the free end section of the first feedback element is transferable to a vibrational state. When stimulated to vibrate the vibration of the free end section of the first feedback element serves to enhance and to amplify an acoustically perceivable signal generated by the mechanical engagement of the first and the second engaging sections.

A vibration of the free end section can be stimulated through the mechanical interaction of the first and the second engaging sections. When in the vibrational state the first feedback element itself may be subject to an acoustically or even haptically perceivable vibration. The vibration of the first feedback element, in particular the vibration of its free end section, may amplify an acoustic noise or acoustic sound generated by the mechanical engagement of the first engaging section with the second engaging section. Moreover, the vibration of the first feedback element may serve to strike the sound generator, if the sound generator is provided as a separate part from the first feedback element.

In addition and in some examples, the first feedback element and/or its free end section may comprise a resonance frequency that is in the range of the frequency of an acoustic signal that arises when the first and the second engaging sections mutually engage. In this way, the resonance or the resonant behavior of the first feedback element provides an amplification of an acoustic signal generated by the mutual engagement of the first engaging section and the second engaging section.

In some examples, the first feedback element comprises a body having at least one hollow portion at the free end section. The hollow portion may comprise a resonance frequency or may exhibit an eigenfrequency that substantially matches with the frequency of the acoustic sound generated by the mutual engagement of the first engaging section and the second engaging section. In this way, the hollow portion of the feedback element is configured to provide acoustic amplification of the acoustic signal generated by the first and the second engaging sections.

In some examples, the first feedback element comprises a curved section located between the engaging section and the free end section. The curved section may provide a specific acoustic amplification. The curved section may further have a specific and well-defined resonance frequency in response to mechanical stimulation or mechanical vibration that is e.g. provided by the mutual mechanical engagement of the first engaging section and the second engaging section. Moreover, the curved section may exhibit a well-defined vibrational behavior inducible by the mechanical engagement of the first and the second engaging sections.

The curved section may inherently provide an acoustic amplification of an acoustic signal emanating from the first engaging section. It is even conceivable, that a portion of the curved section, in particular the free end of the curved section is hollow. The curved section may comprise an increasing cross-section or an increasing hollow diameter towards the free end section. In this way the curved section and/or the free end section of the first feedback element may provide a kind of a trumpet bell inherently providing an amplification of audible sound.

In some examples, the free end section comprises a contact surface configured to audibly engage with the sound generator when the first feedback element returns from the biased rates to the initial state. The contact surface may form the very end of the free end section. When for instance the free end section is stimulated to vibrate it is the contact surface that exhibits the largest vibration amplitude of the first feedback element. Providing a maximum vibration amplitude at the free end of the first feedback element is beneficial to strike a separate sound generator. In this way, the mechanical momentum when striking the sound generator can be maximized. In effect, a well-defined and distinguishable sound can be generated by the sound generator.

In some examples, the sound generator is transferable to a vibrational state through engagement with the first feedback element. Here, the first feedback element acts and behaves as a clapper, as a tongue or as a mallet configured to strike the sound generator. Typically, the first feedback element is configured to temporally strike the sound generator so that after a striking event the sound generator is free to vibrate in order to provide a long-lasting substantially undamped slowly attenuating noise or sound.

By providing a sound generator separate from the first and the second feedback element a large variety of different characteristic sounds can be generated and designed. For instance, the sound generator may exhibit a reverb effect. It may provide and exhibit a chime sound or a sound of a bell.

In some configurations, the first feedback element and its free end section is located at a well-defined distance from the separate sound generator when the first feedback element is in its initial state. Striking of the sound generator by returning from the biased state to the initial state may be due to a temporary over shooting of the sound generator beyond the initial state when returning from the biased state towards the initial state.

In some examples, the second feedback element is configured to transfer the first feedback element from the initial state towards and into the biased state. In this way, a relative movement of the first feedback element and the second feedback element serves to transfer the first feedback element from the initial state towards and into the biased state. A further movement of the first feedback element relative to the second feedback element then leads to the returning of the first feedback element into the initial state. Typically, the first feedback element is translationally displaceable relative to the second feedback element or the first feedback element is rotationally displaceable relative to the second feedback element. It is even conceivable, that the first feedback element is both, translationally and rotationally movable relative to the second feedback element. Typically, one of the first and the second feedback elements is stationary during dispensing of a dose of the medicament while the other one of the first and the second feedback elements is subject to a movement.

In some configurations, the first and the second feedback elements are movable relative to each other with respect to a second direction that differs from the first direction along which the first feedback element is movable, pivotable or resiliently deformable. The mutual interaction of the first and the second feedback element may be configured such, that a displacement or movement of the first feedback element relative to the second feedback element along the second direction leads to and induces a movement, a pivoting or a resilient deformation of the first feedback element along the first direction. The first and second directions may be oriented perpendicular to each other.

With a cylindrically shaped injection device it is for instance conceivable that the first feedback element is axially displaceable relative to the second feedback element and that the first feedback element, due to engagement with the second feedback element, is subject to a radial or circumferential pivoting, movement or resilient deformation. In other examples the first feedback element may be rotationally displaceable relative to the second feedback element thus leading to a pivoting, movement or resilient deformation of the first feedback element in circumferential direction or radial direction.

According to some examples, at least one of the first and the second feedback elements comprises a beveled section to engage with the other one of the first and the second feedback elements. Typically, the first feedback element comprises a first beveled section and the second feedback element comprises a second beveled section. The first and the second beveled sections are configured to communicate with each other. The first and the second beveled sections may have complementary shapes. Hence, the first beveled section may communicate and may engage with the second beveled section as the first feedback element is subject to a movement relative to the second feedback element along the second direction. By means of the mutually corresponding first and second beveled sections, the movement of the first feedback element relative to the second feedback element along the second direction leads to a respective movement, a pivoting or a resilient deformation of the first feedback element along the first direction. The degree and magnitude of the movement, the people to an angle or the resilient deformation is governed by the shape of the first and the second beveled sections.

In general it is sufficient when only one of the first and the second feedback elements comprises a single beveled section to engage with a surface or a portion of the other one of the first and the second feedback elements.

In some examples, the first and the second engaging sections are configured to positively engage when the first feedback element reaches the initial state. By means of a positive engagement the first and the second feedback elements can be mutually fixed, e.g. with regards to the second direction. Moreover, by means of mutually corresponding and hence positively engaging first and second engaging sections, a well-defined acoustically perceivable feedback can be provided.

In some examples, at least one of the first and the second engaging sections comprises a recess and the other one of the first and the second engaging section comprises a protrusion. The recess is configured to receive the protrusion when the first feedback element reaches the initial state. Typically, when the protrusion engages the recess it may produce and generate the acoustically perceivable sound and hence an acoustic feedback signal that is amplified by the free end section of the first feedback element and/or by the mechanical engagement with a separate sound generator.

In some examples (e.g., examples without a separate sound generator), it is the mutual engagement of the first and the second engaging sections, e.g. the mutual engagement and mechanical interaction of the recess and the protrusion that generates a sound that is amplified by the free end section of the first feedback element. Typically, the free end section of the first feedback element is unitary or integrally formed with the first engaging section. In this way, a sufficient sound propagating and sound guiding structure can be provided from the first engaging section towards the free end section.

In some examples, the injection device further comprises a housing accommodating the acoustic feedback arrangement. The injection device further comprises a dose tracking member movably arranged inside or movably attached to the housing during dispensing of a dose of the medicament. At least one of the first and the second feedback elements is connected to or integrated into the dose tracking member. The other one of the first and the second feedback elements is then connected to or integrated into the housing. The first and second feedback elements are connected to or integrated into the housing and the dose tracking member so that the first engaging section of the first feedback element engages with the second engaging section of the second feedback element when the dose tracking member reaches an end of dose configuration at the end of a dose dispensing procedure. In this way, the acoustic feedback arrangement provides an acoustic feedback signal at the end of a dose dispensing procedure indicating to a patient or to a user of the injection device that the process of expelling of a liquid medicament has terminated.

The dose tracking member may be movably arranged inside the housing or may be movably attached to the housing also during setting of a dose. Hence, during the process of dose setting the dose tracking member may be subject to a movement along a dose increasing direction. During a subsequent dose injection or dose dispensing procedure the dose tracking member may be subject to a movement along an opposite direction, i.e. along a dose decrementing direction. Accordingly, the dose tracking member is subject to a movement along the second direction during dose dispensing. It may be subject to an oppositely directed movement along the second direction during dose setting.

In some examples, the dose tracking member comprises one of a number sleeve, a clutch member and the drive sleeve rotationally and/or translationally movable relative to the housing during setting of a dose or during dispensing of a dose of the medicament.

In some examples, the injection device further comprises a cartridge filled with the medicament. The cartridge may be arranged inside the housing of the injection device. The cartridge is typically sealed by a bung movably arranged inside a barrel of the cartridge. The bung typically forms a proximal seal of the cartridge while a distal end of the barrel of the cartridge is sealed by a further seal, e.g. by a septum. The distal seal and hence the distal end of the cartridge is typically pierceable by a needle arrangement, such as a double-tipped injection needle.

The injection device further comprises a piston rod movably arranged inside and relative to the housing. The piston rod is typically translationally displaceable relative to the housing in axial direction. It is operably engageable with the bung or piston of the cartridge for expelling of a dose of the medicament from the cartridge, typically through the double-tipped injection needle when attached to the distal end of the cartridge.

The injection device may be configured as a disposable device that is intended to be discarded in its entirety when the content of the medicament provided inside the cartridge has been used up. With a disposable device the cartridge is typically preassembled inside the injection device when delivered to end consumers or patients. The injection device may be also configured as a reusable device providing replacement of an empty cartridge after consumption of its content. Here, a distal housing portion, typically denoted as a cartridge holder, is disconnectable from a proximal housing component so as to enable a replacement of an empty cartridge.

In the present context a distal portion or the distal direction refers to that portion of the injection device that faces towards an injection site or towards biological tissue into which the medicament should be injected. A proximal portion of the proximal direction refers to the opposite direction, facing away from a dispensing end of the injection device.

The injection device is typically configured as a hand held injection pen. The injection device may be implemented all mechanically. It may be user actuatable in that sense that a user has to provide the entirety of a driving force required to drive the bung of the cartridge in distal direction. The injection device may be power assisted in that sense that it comprises a mechanical or electrical energy storage reservoir that is configured to provide a driving force that is contributing to the distally directed displacement of the button of the cartridge. In other examples the injection device may be implemented as an auto injector and/or may comprise an electrically operated drive configured to provide the entirety of a driving force necessary to move the bung relative to the barrel of the cartridge for the purpose of expelling of a dose of the medicament therefrom.

The term "drug" or "medicament", as used herein, means a pharmaceutical formulation containing at least one pharmaceutically active compound, wherein in some embodiments the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in some embodiments the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in some embodiments the pharmaceutically active compound comprises at least one peptide for the treatment and/or prophylaxis of diabetes mellitus or complications associated with diabetes mellitus such as diabetic retinopathy, wherein in some embodiments the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39), des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE FIGURES

In the following, embodiments of the drive mechanism and the injection device are described in detail by making reference to the drawings, in which.

DETAILED DESCRIPTION

Figure 1:
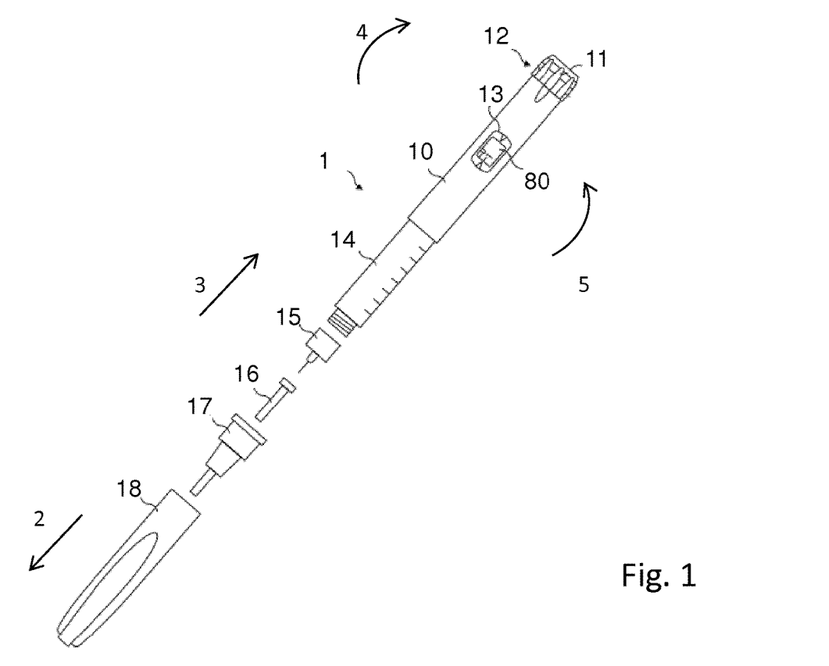
FIG. 1 schematically shows an example of an injection device.
Figure 2:
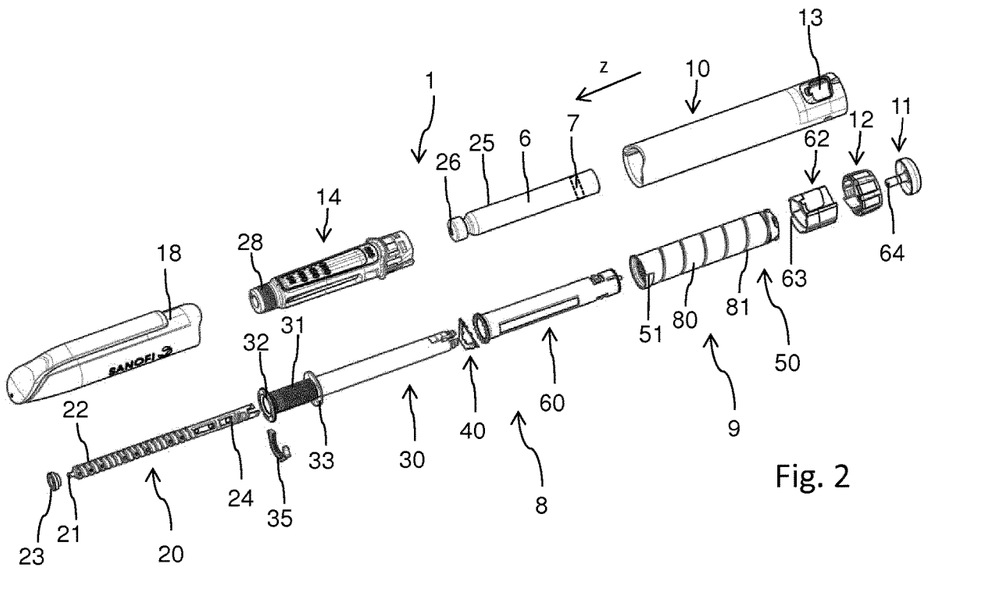
FIG. 2 shows an exploded view of the components of the injection device of FIG. 1.

The injection device 1 as shown in FIGS. 1 and 2 is a pre-filled disposable injection device that comprises a housing 10 to which an injection needle 15 can be affixed. The injection needle 15 is protected by an inner needle cap 16 and either an outer needle cap 17 or a protective cap 18 that is configured to enclose and to protect a distal section of the housing 10 of the injection device 1. The housing 10 may comprise and form a main housing part configured to accommodate a drive mechanism 8 as shown in FIG. 2. The injection device 1 may further comprise a distal housing component denoted as cartridge holder 14. The cartridge holder 14 may be permanently or releasably connected to the main housing 10. The cartridge holder 14 is typically configured to accommodate a cartridge 6 that is filled with a liquid medicament. The cartridge 6 comprises a cylindrically-shaped or tubular-shaped barrel 25 sealed in proximal direction 3 by means of a bung 7 located inside the barrel 25. The bung 7 is displaceable relative to the barrel 25 of the cartridge 6 in a distal direction 2 by means of a piston rod 20. A distal end of the cartridge 6 is sealed by a pierceable seal 26 configured as a septum and being pierceable by a proximally directed tipped end of the injection needle 15. The cartridge holder 14 comprises a threaded socket 28 at its distal end to threadedly engage with a correspondingly threaded portion of the injection needle 15. By attaching the injection needle 15 to the distal end of the cartridge holder 14 the seal 26 of the cartridge 6 is penetrated thereby establishing a fluid transferring access to the interior of the cartridge 6.

When the injection device 1 is configured to administer e.g. human insulin, the dosage set by a dial member 12 at a proximal end of the injection device 1 may be displayed in so-called international units (IU), wherein 1 IU is the biological equivalent of about 45.5 µg of pure crystalline insulin (1/22 mg).

As shown further in FIGS. 1 and 2, the housing 10 comprises a dosage window 13 that may be in the form of an aperture in the housing 10. The dosage window 13 permits a user to view a limited portion of a number sleeve 80 that is configured to move when the dial member 12 is turned, to provide a visual indication of a currently set dose.

The dial member 12 is rotated on a helical path with respect to the housing 10 when turned during setting and/or dispensing or expelling of a dose.

The injection device 1 may be configured so that turning the dosage knob 12 causes a mechanical click sound to provide acoustical feedback to a user. The number sleeve 80, a clutch member and a drive sleeve 30 mechanically interacts with a bung 7 in the insulin cartridge 6 via the piston rod 20. When the needle 15 is stuck into a skin portion of a patient, and when the trigger 11 or injection button is pushed, the insulin dose displayed in display window 13 will be ejected from injection device 1. When the needle 15 of the injection device 1 remains for a certain time in the skin portion after the trigger 11 is pushed, a high percentage of the dose is actually injected into the patient's body. Ejection of an insulin dose may also cause a mechanical click sound or a particular end-of dose sound, which is however different from the sounds produced when using the dial member 12.

In some embodiments, during delivery of the insulin dose, the dial member 12 is turned to its initial position in an axial movement, that is to say without rotation, while the number sleeve 80 is rotated to return to its initial position, e.g. to display a dose of zero units.

The injection device 1 may be used for several injection processes until either the cartridge 6 is empty or the expiration date of the medicament in the injection device 1 (e.g. 28 days after the first use) is reached.

Furthermore, before using injection device 1 for the first time, it may be necessary to perform a so-called "prime shot" to remove air from the cartridge 6 and the needle 15, for instance by selecting two units of the medicament and pressing trigger 11 while holding the injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user.

The expelling or drive mechanism 8 as illustrated in more detail in FIG. 2 comprises numerous mechanically interacting components. A flange like support of the housing 10 comprises a threaded axial through opening threadedly engaged with a first thread or distal thread 22 of the piston rod 20. The distal end of the piston rod 20 comprises a bearing 21 on which a pressure foot 23 is free to rotate with the longitudinal axis of the piston rod 20 as an axis of rotation. The pressure foot 23 is configured to axially abut against a proximally facing thrust receiving face of the bung 7 of the cartridge 6. During a dispensing action the piston rod 20 rotates relative to the housing 10 thereby experiencing a distally directed advancing motion relative to the housing 10 30 and hence relative to the barrel 25 of the cartridge 6. As a consequence, the bung 7 of the cartridge 6 is displaced in distal direction 2 by a well-defined distance due to the threaded engagement of the piston rod 20 with the housing 10.

The piston rod 20 is further provided with a second thread 24 at its proximal end. The distal thread 22 and the proximal thread 24 are oppositely handed.

There is further provided the drive sleeve 30 having a hollow interior to receive the piston rod 20. The drive sleeve 30 comprises an inner thread threadedly engaged with the proximal thread 24 of the piston rod 20. Moreover, the drive sleeve 30 comprises an outer threaded section 31 at its distal end. The threaded section 31 is axially confined between a distal flange portion 32 and another flange portion 33 located at a predefined axial distance from the distal flange portion 32. Between the two flange portions 32, 33 there is provided a last dose limiting member 35 in form of a semi-circular nut having an internal thread mating the threaded section 31 of the drive sleeve 30.

The last dose limiting member 35 further comprises a radial recess or protrusion at its outer circumference to engage with a complementary-shaped recess or protrusion at an inside of the sidewall of the housing 10. In this way the last dose limiting member 35 is splined to the housing 10. A rotation of the drive sleeve 30 in a dose incrementing direction 4 or clockwise direction during consecutive dose setting procedures leads to an accumulative axial displacement of the last dose limiting member 35 relative to the drive sleeve 30. There is further provided an annular spring 40 that is in axial abutment with a proximally facing surface of the flange portion 33. Moreover, there is provided a tubular-shaped clutch member 60. At a first end the clutch member 60 is provided with a series of circumferentially directed saw teeth. Towards a second opposite end of the clutch member 60 there is located a radially inwardly directed flange.

Furthermore, there is provided a dose dial sleeve also denoted as number sleeve 80. The number sleeve 80 is provided outside of the spring 40 and the clutch member 60 and is located radially inward of the housing 10. A helical groove 81 is provided about an outer surface of the number sleeve 80. The housing 10 is provided with the dosage window 13 through which a part of the outer surface of the number sleeve 80 can be seen. The housing 10 is further provided with a helical rib at an inside sidewall portion of an insert piece 62, which helical rib is to be seated in the helical groove 81 of the number sleeve 80. The tubular shaped insert piece 62 is inserted into the proximal end of the housing 10. It is rotationally and axially fixed to the housing 10. There are provided first and second stops on the housing 10 to limit a dose setting procedure during which the number sleeve 80 is rotated in a helical motion relative to the housing 10.

The dose member 12 in form of a dose dial grip is disposed about an outer surface of the proximal end of the number sleeve 80. An outer diameter of the dose member 12 typically corresponds to and matches with the outer diameter of the housing 10. The dose member 12 is secured to the number 80 to prevent relative movement therebetween. The dose member 12 is provided with a central opening.

The trigger 11, also denoted as dose button is substantially T-shaped. It is provided at a proximal end of the injection device 10. A stem 64 of the trigger 11 extends through the opening in the dose member 12, through an inner diameter of extensions of the drive sleeve 30 and into a receiving recess at the proximal end of the piston rod 20. The stem 64 is retained for limited axial movement in the drive sleeve 30 and against rotation with respect thereto. A head of the trigger 11 is generally circular. The trigger side wall or skirt extends from a periphery of the head and is further adapted to be seated in a proximally accessible annular recess of the dose member 12.

To dial a dose a user rotates the dose member 12. With the spring 40 also acting as a clicker and the clutch member 60 engaged, the drive sleeve 30 the spring or clicker 40, the clutch member 60 and the number sleeve 80 rotate with the dose member 12. Audible and tactile feedback of the dose being dialed is provided by the spring 40 and by the clutch member 60. Torque is transmitted through saw teeth between the spring 40 and the clutch member 60. The helical groove 81 on the number sleeve 80 and a helical groove in the drive sleeve 30 have the same lead. This allows the number sleeve 80 to extend from the housing 10 and the drive sleeve 30 to climb the piston rod 20 at the same rate.

At a limit of travel a radial stop on the number sleeve 80 engages either with a first stop or a second stop provided on the housing 10 to prevent further movement. Rotation of the piston rod 20 is prevented due to the opposing directions of the overall and driven threads on the piston rod 20.

The last dose limiting member 35 keyed to the housing 10 is advanced along the threaded section 31 by the rotation of the drive sleeve 30. When a final dose configuration or position is reached, a radial stop formed on a surface of the last dose limiting member 35 abuts a radial stop on the flange portion 33 of the drive sleeve 30, preventing both, the last dose limiting member 35 and the drive sleeve 30 from rotating further.

Should a user inadvertently dial beyond the desired dosage, the injection device 1, configured as a pen-injector allows the dosage to be dialed down without dispense of the medicament from the cartridge 6. For this the dose member 12 is simply counter-rotated. This causes the system to act in reverse. A flexible arm of the spring or clicker 40 then acts as a ratchet preventing the spring 40 from rotating. The torque transmitted through the clutch member 60 causes the saw teeth to ride over one another to create the clicks corresponding to dialed dose reduction. Typically, the saw teeth are so disposed that a circumferential extent of each saw tooth corresponds to a unit dose.

When the desired dose has been dialed the user may simply dispense the set dose by depressing the trigger 11. This displaces the clutch member 60 axially with respect to the number sleeve 80 causing dog teeth thereof to disengage. However, the clutch member 60 remains keyed in rotation to the drive sleeve 30. The number sleeve 80 and the dose member 12 are now free to rotate in accordance with the helical groove 81.

The axial movement deforms the flexible arm of the spring 40 to ensure the saw teeth cannot be overhauled during dispense. This prevents the drive sleeve 30 from rotating with respect to the housing 10 though it is still free to move axially with respect thereto. The deformation is subsequently used to urge the spring 40 and the clutch member 60 back along the drive sleeve 30 to restore the connection between the clutch member 60 and the number sleeve 80 when the distally directed dispensing pressure is removed from the trigger 11.

The longitudinal axial movement of the drive sleeve 30 causes the piston rod 20 to rotate through the through opening of the support of the housing 10, thereby to advance the bung 7 in the cartridge 6. Once the dialed dose has been dispensed, the number sleeve 80 is prevented from further rotation by contact of a plurality of members extending from the dose member 12 with a corresponding plurality of stops. A zero dose position is finally determined by the abutment of one of axially extending edges of members of the number indicating sleeve 80 with a corresponding stop of the housing 10.

The dose setting mechanism 9 as illustrated in FIG. 2 comprises at least the dial member 12 and the number sleeve 80. As the dial member 12 is rotated during and for setting of a dose the number sleeve 80 starts to rotate relative to the housing 10 along a helical path as defined by the threaded engagement of its outer thread or helical groove 81 with a correspondingly shaped threaded section at the inside surface of the housing 10.

During dose setting and when the drive mechanism 8 or the dose setting mechanism 9 is in the dose setting mode the drive sleeve 30 rotates in unison with the dial member 12 and with the number sleeve 80. The drive sleeve 30 is threadedly engaged with the piston rod 20, which during dose setting is stationary with regard to the housing 10. Accordingly, the drive sleeve 30 is subject to a screwing or helical motion during dose setting. The drive sleeve 30 starts to travel in proximal direction as the dose dial member is rotated in a dose incrementing direction 4, e.g. in a clockwise direction. For adjusting of or correcting a size of a dose the dial member 12 is rotatable in an opposite direction, hence in a dose decrementing direction 5, e.g. counterclockwise.

At least one of the drive sleeve 30, the clutch member 60 and the number sleeve 80 serves as a dose tracking member 50 that may comprise a tracking stop feature 51. In some examples, such as the example as illustrated for instance in FIG. 2, one of the flanges 32 or 33 provides and coincides with a tracking stop feature 51 of the dose tracking member 50.

The dose setting and expelling mechanism or drive mechanism 8 as described above is only exemplary for one of a plurality of differently configured drive mechanisms that are generally implementable in a disposable pen-injector and with an acoustic feedback arrangement as will be described below. The drive mechanism as described above is explained in more detail e.g. in WO2004/078239A1, WO 2004/078240A1 or WO 2004/078241A1 the entirety of which being incorporated herein by reference.

Figure 3:
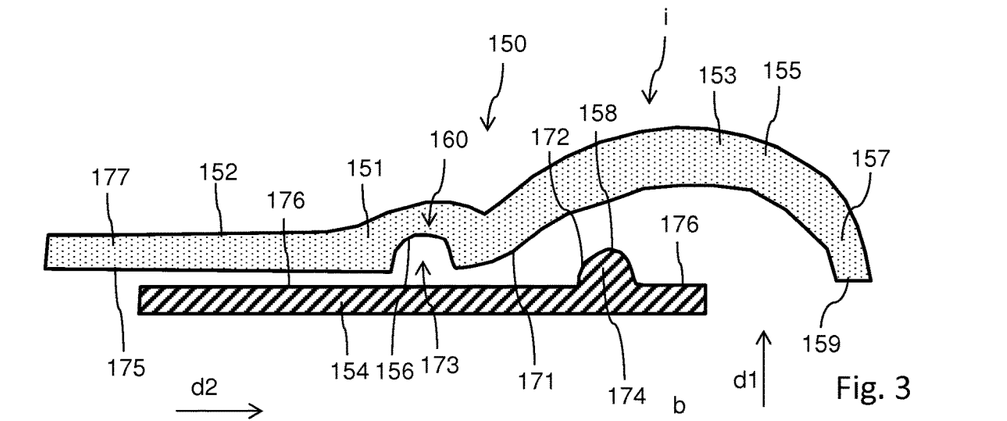
FIG. 3 shows a side view of an example of the acoustic feedback arrangement with the first feedback arrangement in an initial state.
Figures 4, 5:
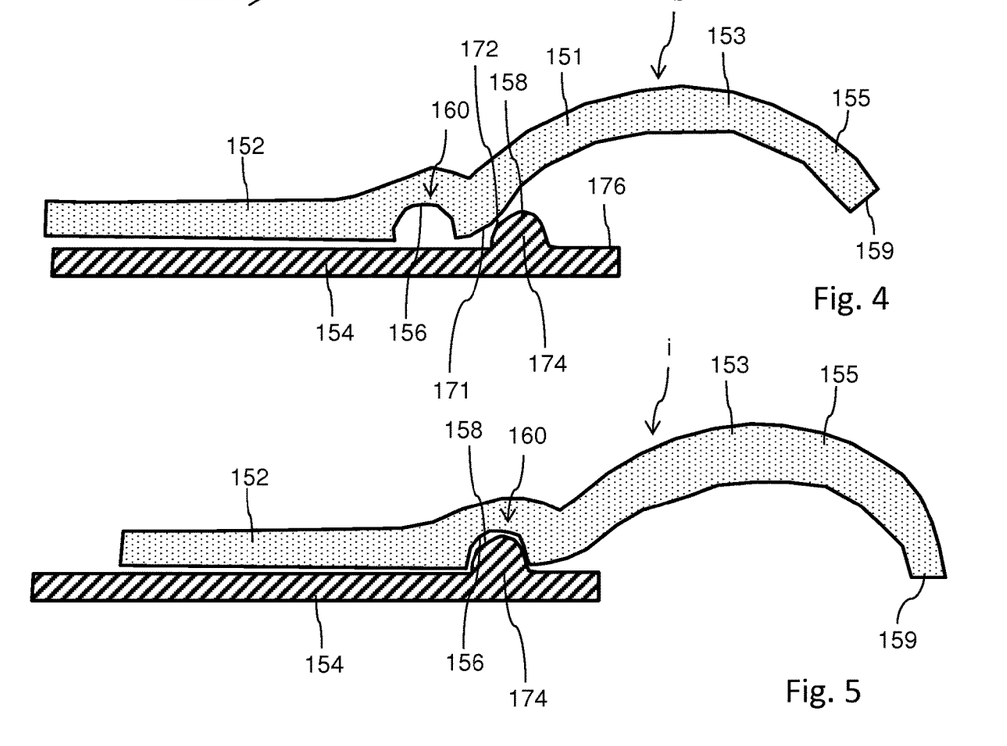
FIG. 4 shows a configuration of the acoustic feedback arrangement according to FIG. 3 with the first feedback arrangement in a biased state.
FIG. 5 shows a configuration of the acoustic feedback arrangement according to FIGS. 3 and 4 after the first feedback arrangement having returned into the initial state.
Figure 6:
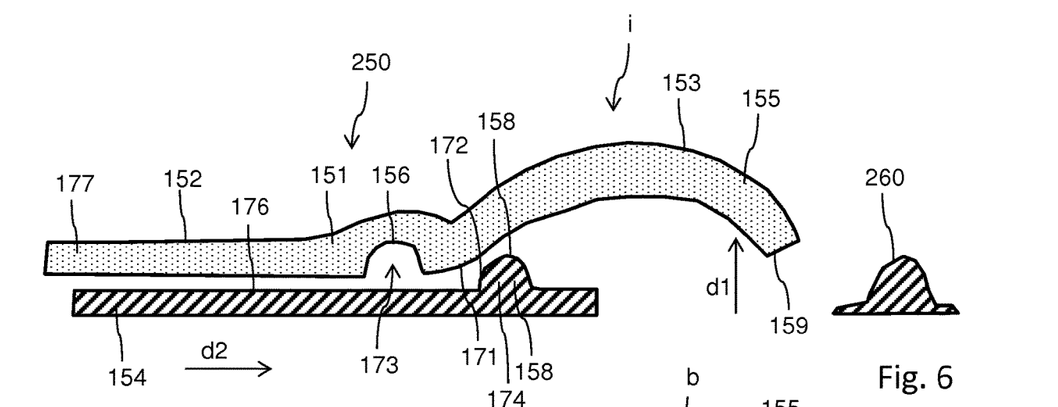
FIG. 6 shows a side view of another example with a separate sound generator and with the first feedback element in an initial state.

The injection device 1 further comprises an acoustic feedback arrangement 150, 250 as will be explained in greater detail with regard to FIGS. 3 to 9. In general, at least one of the drive sleeve 30, the clutch member 60 and the number sleeve 80 may serve and provide a dose tracking member 50 having one of a first and a second feedback element 152, 154 of the acoustic feedback arrangement 150 as illustrated in FIGS. 3 to 5. A stationary component of the injection device 1, such as the housing 10 or the insert piece 62 may have or may be equipped with the other one of a first and the second feedback element 152, 154 of the acoustic feedback arrangement 150.

As illustrated by the sequence of FIGS. 3, 4 and 5 the first feedback element 152 is movable relative to the second feedback element 154. The first feedback element 152 may be translationally and/or rotationally movable relative to the second feedback element 154 with regards to a second direction d2. As it is immediately apparent from a comparison of FIGS. 3 and 4 the first feedback element 152 is resiliently deformable with regards to a first direction d1. In the presently illustrated example the first direction d1 and the second direction d2 are oriented perpendicular with regard to each other. The first direction d1 may be oriented radially inwardly or radially outwardly with regards to the overall tubular shape of the housing 10. The first direction d1 may be also oriented in circumferential or tangential direction with regards to the overall tubular shape of the housing 10. The second direction d2 may be oriented in axial direction with regards to the tubular shape of the housing 10. It may coincide with the distal direction 2 or with the proximal direction 3 as indicated in FIG. 1.

It is also conceivable, that the second direction d2 is oriented tangentially or circumferentially and that the first direction d1 is oriented radially inwardly or radially outwardly.

In some examples, such as the examples of FIGS. 3 to 5, the first feedback element 152 is slidably and continuously displaceable relative to the second feedback element 154. The first feedback element 152 comprises a first engaging section 156, e.g. in form of a recess 173. Correspondingly, the second feedback element 154 comprises a second engaging section 158, e.g. in form of a protrusion 174. The protrusion 174 is shaped to fit into the recess 173. In this way and when reaching an end-of-dose configuration as shown in FIG. 5, the protrusion 174 is entirely received in the recess 173. The configuration as shown in FIG. 5 corresponds to a zero dose configuration, at the end of a dose dispensing procedure conducted by the injection device 1.

Prior to reach the zero dose configuration the first engaging section 156 of the first feedback element 152 approaches the second engaging section 158 of the second feedback element 154. While approaching the second engaging section 158 the first feedback element 152 is subject to a resilient deformation. Since the first and second feedback elements 152, 154 are fixed inside the housing or are fixedly attached to the housing 10 with regard to the first direction d1 a movement of the first feedback element 152 towards the zero dose configuration is accompanied by a resilient deformation at least of a portion of the first feedback element 152.

As shown in FIG. 4, a first beveled section 171 at a side face of the first feedback element 152 facing towards the second feedback element 154 gets in abutment with the protrusion 174. The protrusion 174 of the second feedback element 154 comprises a correspondingly shaped second beveled section 172. As the beveled sections 171, 172 of the first and the second feedback elements 152, 164 mutually engage the first feedback element 152 become subject to a resilient deformation along the first direction d1.

During the course of a further movement of the first feedback element 152 along the second direction d2 relative to the second feedback element 154, the degree of resilient deformation increases until the first engaging section 156, e.g. the recess 173 of the first feedback element 152 engages with the second engaging section 158, e.g. the protrusion 174 of the second feedback element 154. During the resilient deformation of the first feedback element 152 along the first direction d1 the first feedback element 152 is mechanically biased or pre-tensed. As indicated in FIG. 4, the first feedback element 152 is in a biased state b. As soon as the first and the second engaging sections 156, 158 are in a position to mutually engage, the biased section or the resiliently deformed section of the first feedback element 152 suddenly dislodges and returns into an initial state i as shown in FIGS. 3 and 5.

The first feedback element 152 comprises a resiliently deformable body 151 that is deformable from the initial state i as shown in FIG. 3 into a biased state b as shown in FIG. 4. The body 151 provides a resilient restoring force. As the first feedback element 152 returns into its initial state i under the effect of the resilient restoring force it produces an audible sound or an audible noise when engaging with the second feedback element 154.

As it is further shown in FIGS. 3 to 5 the first feedback element 152, in particular its body 151 comprises a free end section 155 that is located at a distance from the first engaging section 156. The free end section 155 is free of contact to the second feedback element 154 in either configuration. The free end section 155 is permanently void of any mechanical contact to the second feedback element 154 or to any other component of the injection device 1. In this way, the free end section 155 is free to vibrate as the first engaging section 156 audibly engages with the second engaging section 158. In this way, a noise or a sound generated by the mutual and mechanical interaction of the first and the second engaging sections 156, 158 is not only transferable towards and into the free end section 155. Due to the freely vibrating suspension of the free end section 155, an acoustic noise or an acoustic sound generated by the first and the second engaging sections 156, 158 can be enhanced and amplified by the vibration of the free end section 155. At least, the free end section 155 may provide a kind of a reverb effect and a comparatively long-lasting and comparatively slowly attenuating characteristic end-of-dose sound can be generated.

The free end section 155 of the first feedback element 152 may comprise a curved section 153. The curved section 153 may comprise an arc-shape, wherein in the initial state i of the first feedback element 152 a free end or a contact surface 159 at the free end of the free end section 155 is approximately located at the same level with regards to the first direction d1 than a surface portion 175 of a base portion 177 of the first feedback element 152. Here, the surface portion 175 is located on a side of the first feedback element that faces towards the second feedback element as seen along the first direction d1.

In the biased state b as shown in FIG. 4 the free end section 155 and the contact surface 159 comprise a larger distance to a surface portion 176 of the second feedback element 154 that faces towards the first feedback element 152. As the first and the second feedback elements 152, 154 mutually engage with their first and second engaging sections 156, 158 the surface portions 175, 176 of the first and the second feedback elements 152, 154 mutually approach compared to the biased state of the first feedback element 152.

At least a portion of the free end section 155, in particular the very end of the free end section 155 may comprise a hollow portion 157. In that part of the free end section of the body 151 of the first feedback element 152 may be of substantially hollow shape. A hollow shape of the curved section 153 of the free end section 155 may further enhance an acoustic amplification of an audible for acoustic signal generated by the mechanical engagement of the first and the second engaging sections 156, 158.

Additionally or alternatively it is also conceivable, that the surface portions 175, 176 of the first and the second feedback elements 152, 154 that face towards each other mutually and audibly engage as the first feedback element 152 returns from the biased state b into the initial state i. As indicated in FIG. 5, the surface portion 175 of the base portion 177 of the first feedback element 152 almost entirely overlaps with the surface portion 176 of the second feedback element 154. Due to a large overlap, a correspondingly loud or intense acoustic signal can be generated. The acoustic signal may resemble a whip sound or a crack of a whip. Also this sound and the respective sound propagation can be acoustically amplified and enhanced by the shape and the freely vibrating free end section 155 of the first feedback element 152.

In some examples, such as the example of an acoustic feedback arrangement 150 according to FIGS. 3 to 5, the first engaging section 156 forms or contributes to a sound generator 160 that is configured and enabled to produce an audible sound as a zero dose configuration of the first and the second feedback elements 152, 154 has been reached. The free end section 155 of the first feedback element 152 then serves as an acoustic amplification means. In effect and in comparison to solutions known in the art a comparatively load and rather specific acoustic feedback can be provided as the drive mechanism 8 or the dose setting mechanism 9 arrives at the end-of-dose configuration.

In some examples, such as the example of another acoustic feedback arrangement 250 as shown in FIGS. 6 to 9, the first and the second feedback elements 152, 154 remain substantially unchanged compared to the example of the acoustic feedback arrangement 150 as illustrated in FIGS. 3 to 5. But there, a separate sound generator 260 is provided. The sound generator 260 may be located at a well-defined position inside the housing 10 of the injection device 1. Alternatively, the sound generator 260 may be connected to or may be integrally formed with the second feedback element 154. Further alternatively, It may be also connected to or integrally formed with the first feedback element 152, e.g. with the base portion 177 thereof.

Figures 7, 8, 9:
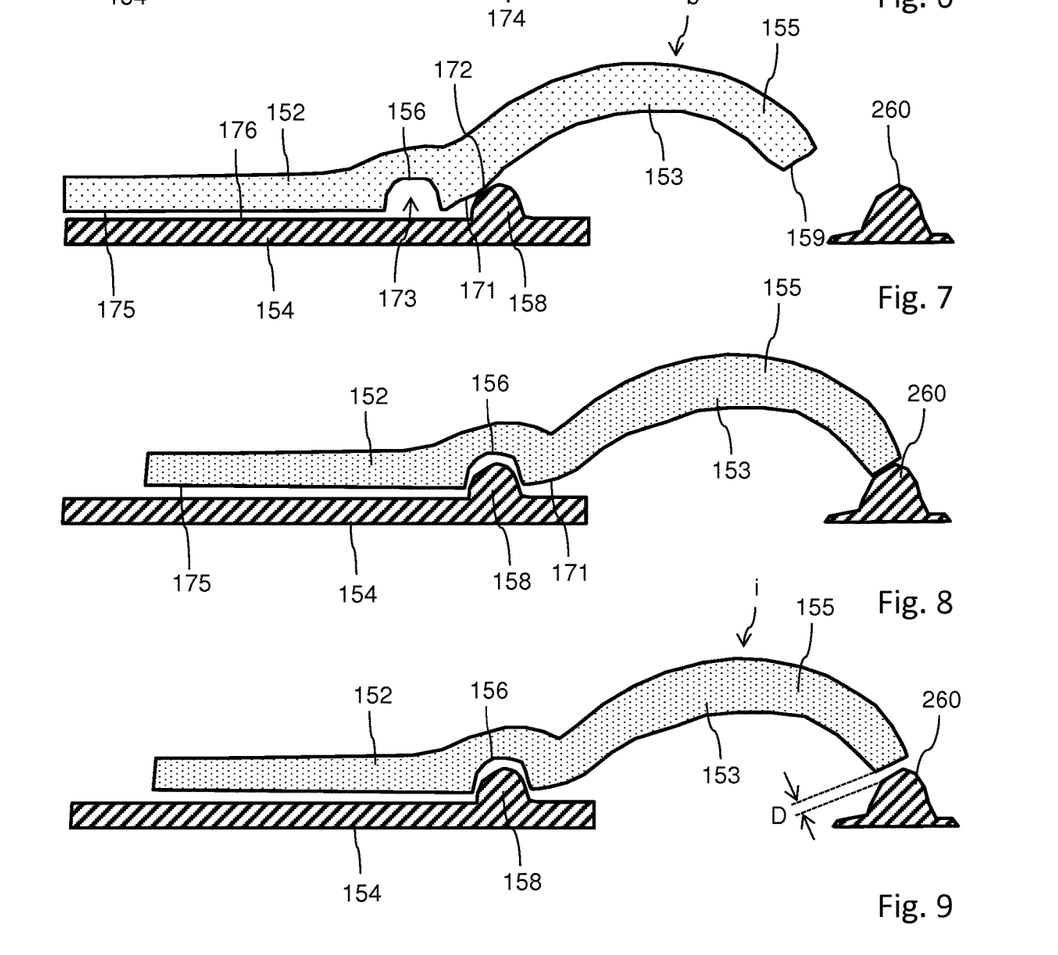
FIG. 7 shows the example according to FIG. 6 with the first feedback element in the biased state.
FIG. 8 shows the example according to FIGS. 6 and 7 when the first feedback element relaxes into the initial state and overshoots the initial state thereby engaging with the sound generator.
FIG. 9 shows the acoustic feedback arrangement of FIGS. 6 to 8 after the first feedback element has relaxed into its initial state.

Upon reaching a zero dose configuration as shown in FIGS. 8 and 9 the free end section 155 of the first feedback element 152 strikes the sound generator 260 in order to generate a distinct and well-defined acoustic feedback signal. The sound generator 260 may comprise a bell shape or may provide a bell function when hit by the contact surface 159 of the free end section 155 of the first feedback element 152. Here, the elastically deformable first feedback element 152 provides the function of a clapper, of a tongue or of a mallet to strike the sound generator 260. As shown in FIG. 7, the free end section 155 of the first feedback element 152 is elastically biased or pre-tensed along the first direction d1 away from the sound generator 260.

As the end of dose configuration as shown in FIG. 8 has been reached, the pre-tensed and biased free end section 155 is abruptly dislodged. Under the effect of a restoring force the base portion 177 of the first feedback element 152 approaches the second feedback element 154. The first and the second feedback elements 152, 154 mutually engage and align with their base portions 177. Since the free end section 155 protrudes from an end section of the second feedback element 154 along the second direction d2 the free end section 155 overshoots the initial state i as shown in FIG. 9 and hits the sound generator 260. When reaching the initial state i, in which the mechanical vibration of the free end section 155 has been attenuated the free end section 155 and the contact surface 159 thereof are located at a well-defined distance D from the sound generator 260. In this way, the sound generator 260 may still vibrate to generate a long-lasting acoustic feedback, e.g. with a reverb effect. The sound generator 260 may be vibrationally supported or suspended inside the housing 10.

In some examples, such as the example according to FIGS. 6 to 9, is not generally necessary, that the second feedback element 154 is located on the same side of the first feedback element 152 as the sound generator 260. It is generally conceivable, that the second feedback element 154 is located at a side of the first feedback element 152 that faces away from the sound generator 260. However, the first and the second feedback elements 152, 154 comprise first and second and mutually corresponding engaging sections 156, 158 so that the first feedback element 154 becomes resiliently deformed, moved of pivoted along the first direction in response to a movement of the first feedback element 152 relative to the second feedback element 154.

Even though it is illustrated in FIGS. 6 to 9 that the first feedback element 152 is displaceable along the second direction d2 relative to the sound generator 260, while the sound generator 260 is fixed relative to the second feedback element 154 it is also conceivable, that the first feedback element 152 is fixed to the sound generator 260 with regards to the second direction d2 and that the first feedback element 152 is only displaceable or pivotable or deformable relative to the sound generator 260 with regard to the first direction d1. Then, it may be the second feedback element 154 that is displaceable relative to the first feedback element 152 with regard to one of the first direction d1 and the second direction d2.

Even though with the illustrated example the first feedback element 152 is resiliently deformable it is likewise conceivable, that the first feedback element 152 is pivotally or movably displaced inside the housing 10 along the first direction d1 so as to swivel or to pivot between the initial state i and the biased state b. In that case, the first feedback element may be coupled with a separate restoring element, such as a spring element or the like resiliently deformable element being deformable against a restoring force.

LIST OF REFERENCES 1 injection device
2 distal direction
3 proximal direction
4 dose incrementing direction
5 dose decrementing direction
6 cartridge
7 bung
8 drive mechanism
9 dose setting mechanism
10 housing
11 trigger
12 dial member
13 dosage window
14 cartridge holder
15 injection needle
16 inner needle cap
17 outer needle cap
18 protective cap
20 piston rod
21 bearing
22 first thread
23 pressure foot
24 second thread
25 barrel
26 seal
28 threaded socket
30 drive sleeve
31 threaded section
32 flange
33 flange
35 last dose limiting member
40 spring
50 dose tracking member
51 tracking stop feature
60 clutch member
62 insert piece
63 stop feature
64 stem
80 number sleeve
81 groove
150 acoustic feedback arrangement
151 body
152 feedback element
153 curved section
154 feedback element
155 free end section
156 engaging section
157 hollow portion
158 engaging section
159 contact surface
160 sound generator
171 beveled section
172 beveled section
173 recess
174 protrusion 175 surface portion
176 surface portion
177 base portion
250 acoustic feedback arrangement
260 sound generator

The invention claimed is:

1. An injection device for setting and injecting of a dose of a medicament, the injection device comprising:
   an acoustic feedback arrangement comprising:
      a first feedback element having a first engaging section and having a free end section located at a predetermined distance from the first engaging section;
      a second feedback element having a second engaging section configured to engage with the first engaging section;
   wherein the first feedback element is movable, pivotable or resiliently deformable along a first direction relative to the second feedback element from an initial state towards a biased state; and
      a sound generator formed by the first engaging section, wherein the first engaging section is configured to mechanically and audibly engage with the second engaging section when the first feedback element returns from the biased state to the initial state; or
      a sound generator mechanically and audibly engageable with the free end section of the first feedback element, wherein the free end section comprises a contact surface configured to mechanically and audibly engage with the sound generator when the first feedback element returns from the biased state to the initial state.

2. The injection device according to claim 1, wherein the free end section of the first feedback element is free of contact to any other component of the injection device when the first feedback element is in the initial state.

3. The injection device according to claim 2, wherein the free end section of the first feedback element is transferable to a vibrational state.

4. The injection device according to claim 1, wherein the free end section of the first feedback element is transferable to a vibrational state.

5. The injection device according to claim 4, wherein the first feedback element comprises a body having at least one hollow portion at the free end section.

6. The injection device according to claim 1, wherein the first feedback element comprises a body having at least one hollow portion at the free end section.

7. The injection device according to claim 1, wherein the first feedback element comprises a curved section located between the first engaging section and the free end section.

8. The injection device according to claim 1, wherein the sound generator is transferable to a vibrational state through engagement with the first feedback element when the sound generator is audibly engageable with the free end section of the first feedback element.

9. The injection device according to claim 1, wherein the second feedback element is configured to transfer the first feedback element from the initial state towards the biased state.

10. The injection device according to claim 1, wherein at least one of the first feedback element and the second feedback element comprises a beveled section to engage with the other one of the first feedback element and the second feedback element.

11. The injection device according to claim 1, wherein the first engaging section and the second engaging section are configured to positively engage when the first feedback element reaches the initial state.

12. The injection device according to claim 1, wherein one of the first engaging section and the second engaging section comprises a recess and wherein the other one of the first engaging section and the second engaging section comprises a protrusion, wherein the recess is configured to receive the protrusion when the first feedback element reaches the initial state.

13. The injection device according to claim 1, further comprising a housing accommodating the acoustic feedback arrangement and a dose tracking member movably arranged inside the housing or movably attached to the housing during dispensing of the dose of the medicament, wherein one of the first and the second feedback elements is connected to or integrated into the dose tracking member and wherein the other one of the first and the second feedback elements is connected to or integrated into the housing.

14. The injection device according to claim 13, wherein the dose tracking member comprises one or more of a number sleeve, a clutch member, or a drive sleeve and wherein the dose tracking member is one or both of rotationally or translationally movable relative to the housing during setting of the dose or during dispensing of the dose of the medicament.

15. The injection device of claim 14, further comprising:
   a cartridge configured to be filled with the medicament, wherein the cartridge is arranged inside the housing and sealed by a bung movably arranged inside a barrel of the cartridge; and
   a piston rod movably arranged inside and relative to the housing and operably engageable with the bung for expelling of the dose of the medicament from the cartridge.

16. The injection device of claim 15, wherein the cartridge is at least partially filled with the medicament.

17. The injection device according to claim 13, further comprising:
   a cartridge filled with the medicament, wherein the cartridge is arranged inside the housing and sealed by a bung movably arranged inside a barrel of the cartridge; and
   a piston rod movably arranged inside and relative to the housing and operably engageable with the bung for expelling of the dose of the medicament from the cartridge.

* * * * *